United States Patent
Stavsky et al.

(10) Patent No.: US 8,763,651 B2
(45) Date of Patent: Jul. 1, 2014

(54) DOSAGE DISPENSING DEVICE

(75) Inventors: Mor Stavsky, Haifa (IL); Gilad Einy, Haifa (IL)

(73) Assignee: Rescue Dose Ltd., Haifa (IL)

( * ) Notice: Subject to any disclaimer, the term of this patent is extended or adjusted under 35 U.S.C. 154(b) by 250 days.

(21) Appl. No.: 12/355,107

(22) Filed: Jan. 16, 2009

(65) Prior Publication Data
US 2009/0198208 A1 Aug. 6, 2009

Related U.S. Application Data

(60) Provisional application No. 61/006,825, filed on Feb. 1, 2008.

(51) Int. Cl.
*B65B 31/00* (2006.01)
*B65B 3/00* (2006.01)

(52) U.S. Cl.
CPC ...................... *B65B 3/003* (2013.01)
USPC ............... 141/27; 141/18; 141/25; 141/329; 225/93; 700/245

(58) Field of Classification Search
USPC ............ 141/21–27, 2; 600/300; 604/123, 199
See application file for complete search history.

(56) References Cited

U.S. PATENT DOCUMENTS

| 4,417,679 A | * | 11/1983 | Shields | 225/93 |
| 5,868,710 A | * | 2/1999 | Battiato et al. | 604/123 |
| 6,159,183 A | * | 12/2000 | Neer et al. | 604/189 |
| 6,604,903 B2 | * | 8/2003 | Osborne et al. | 414/411 |
| 2004/0088951 A1 | * | 5/2004 | Baldwin et al. | 53/425 |
| 2004/0103951 A1 | * | 6/2004 | Osborne et al. | 141/27 |
| 2006/0136095 A1 | * | 6/2006 | Rob et al. | 700/245 |
| 2006/0161459 A9 | * | 7/2006 | Rosenfeld et al. | 705/3 |
| 2007/0125442 A1 | * | 6/2007 | Tribble et al. | 141/27 |
| 2009/0038709 A1 | * | 2/2009 | VanVreeland et al. | 141/18 |

FOREIGN PATENT DOCUMENTS

| WO | PCT/NL2005/000197 | * 10/2006 | B65B 3/04 |
| WO | PCT/NL2006/000197 | * 10/2006 | B65B 3/04 |

* cited by examiner

*Primary Examiner* — Jason Boeckmann
*Assistant Examiner* — Joel Zhou
(74) *Attorney, Agent, or Firm* — William H. Dippert; Eckert Seamans Cherin & Mellott, LLC

(57) ABSTRACT

A dosage dispenser according to the invention is intended to provide a solution for measuring and dilution of liquid medications and issuing marked and ready for use. The dosage dispenser device carries out actions required for the preparation of a required dose of medication, including identifying ampoules, breaking them, filling a syringe, diluting the medication in a solution, marking the syringe, disposing of waste and documenting the process, all at the patient bedside. The dosage dispenser is aimed at reducing the number of errors in the dosage, which is a problem, menacing medical services throughout the world. The problem is made acute by considerable pressure on the medical teams while carrying out many and complex procedures under pressure in a situation of uncertainty and with variable data.

7 Claims, 10 Drawing Sheets

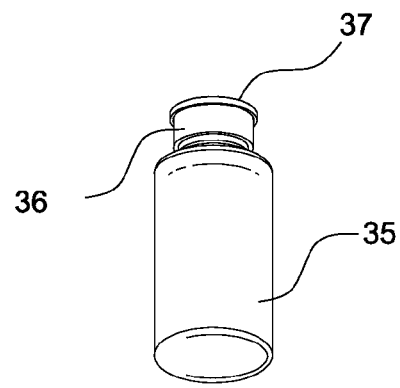
Fig. 3a
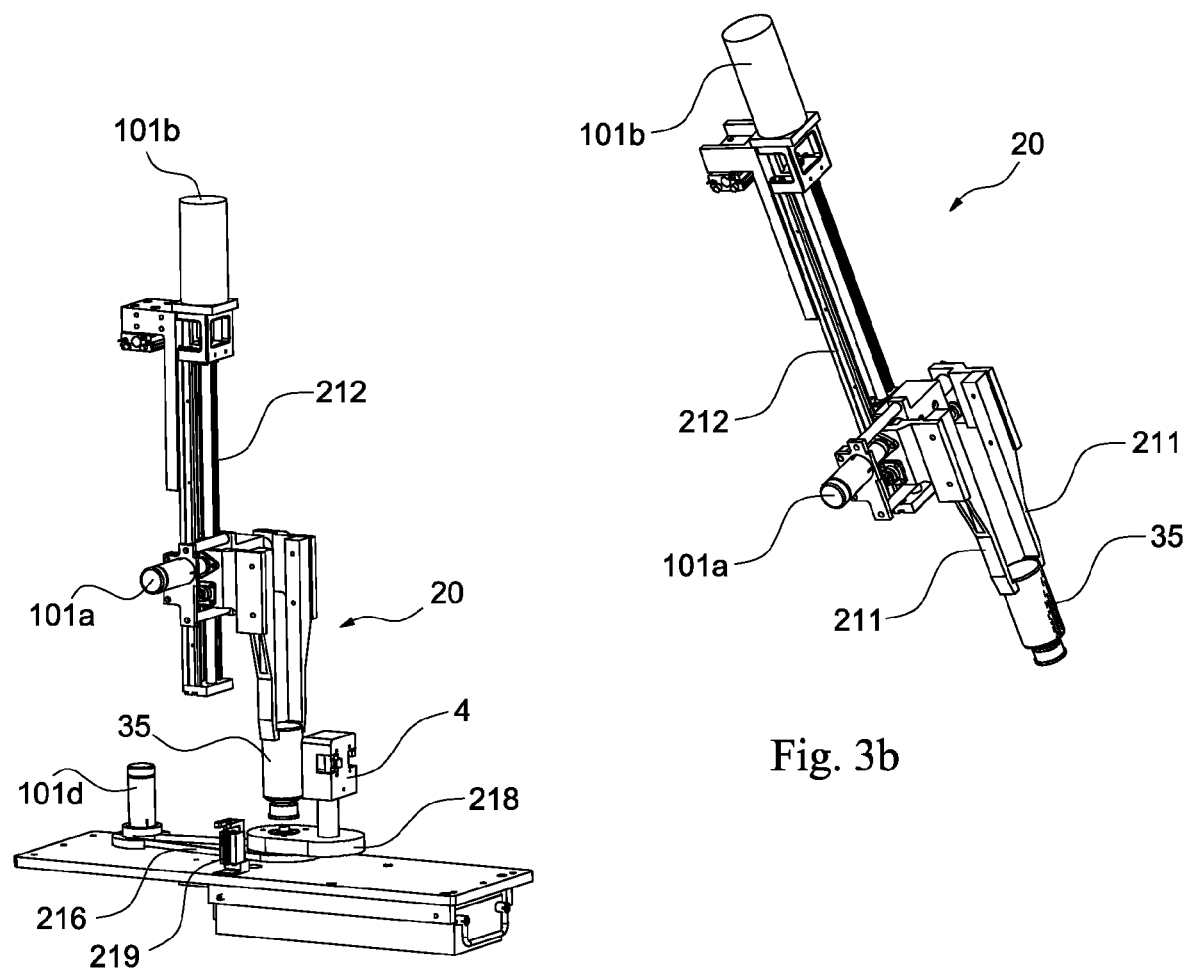
Fig. 3b
Fig. 3c

DOSAGE DISPENSING DEVICE

FIELD OF THE INVENTION

The present invention relates to a dosage dispenser apparatus configured to be located at patient bedside, optionally integrated with monitoring systems for measuring and optionally diluting liquid medications and dispensing marked and ready for use syringes filled with the medication.

The present invention claims the benefit of earlier U.S. Provisional Patent Application Ser. No. 61/006,825, filed Feb. 1, 2008.

BACKGROUND OF THE INVENTION

Many serious errors occur during drug delivery, and specifically, during a high stress situation as in a resuscitation situation. Stress and the need for preparing the drug dose in a hurry increases the potential for errors. Many errors in intravenous (I.V.) drug administration are fatal.

It is one object of the present invention to reduce the number of medication dosage errors, reduce potential for human error, especially in critical situations like resuscitation and trauma care.

Closest Known Related Technology:

There are systems that provide a solution for dosing and dilute I.V. medication. These systems are of large scale designs and are located at the main hospital pharmacy, they are not portable and not adopted to be used at bedside location, and they are incapable of using patient life signs or using medication that are packed in ampoules (a standard package).

For example, U.S. Application 2005/224137 entitled "Device for Reconstituting a Drug Vial and Transferring the Contents to a Syringe in an Automated Matter" by Tribble, et al, discloses an automated medication preparation system in the form of an automated syringe preparation that includes reconstitution of the medication and delivery of the reconstituted medication to a syringe. The system includes an automated fluid delivery device that is movable in at least one direction and is adapted to perform at least one of the following operations: (1) receiving and discharging diluents from a diluents supply in a prescribed amount to reconstitute the medication in a drug vial; and (2) aspirating and later discharging reconstituted medication from the drug vial into the syringe. The system also includes a transfer device that includes a first section for piercing the septum of the drug vial and a second section for sealing, yet releasably, mating with the fluid delivery device. The transfer device is constructed so that it remains within the drug vial for multiple uses without the need to pierce the septum more than one time and therefore, the disadvantages associated with the prior art are overcome. The transfer device has a first channel extending through the first and second sections for carrying diluents or reconstituted medication and a second channel that is in fluid communication with a vent that is formed as part of the transfer device to permit air to flow into the drug vial.

For example U.S. Application No. 2006/0178578 entitled "Vision System To Calculate A Fluid Volume In A Container" by Tribble, et al, discloses a system for calculating a volume of fluid that is disposed within a container. The system includes (1) an imaging device that captures and stores an image of at least the volume of fluid in the container; (2) a background disposed behind the container so that at least the volume of fluid in the container is disposed in front of the background; and (3) a processor that performs at least one operation on the stored image to calculate the volume of the fluid within the container.

U.S. Pat. No. 6,070,761 entitled "Vial Loading Method And Apparatus For Intelligent Admixture And Delivery Of Intravenous Drugs" by Bloom, et. al., discloses a vial-loading mechanism for a system that prepares and delivers one or more IV drugs to a patient. The vial-loading mechanism is used to load a vial onto a cassette spike and includes a vertical support member located adjacent to the spike. A holding assembly holds at least one vial. The holding assembly is mounted to the support member so as to be positioned between an upper position for loading a vial and a lower position for piercing the vial with a spike. The holding assembly has an arcuate-shaped holding member for holding the vial. A catch is provided with an engagement unit for securing the holding assembly in the lower position. This arrangement provides an easy way to add, retain, and remove vials from the system and protects the clinicians that do this from contacting the spikes and hurting themselves.

U.S. Pat. No. 7,163,035 to Khan, et al, entitled "Automated Use Of A Vision System To Detect Foreign Matter In Reconstituted Drugs Before Transfer To A Syringe" describes an automated medication preparation system including automated syringe preparation that involves reconstitution of the medication. The system includes: an automated device for delivering a prescribed unit dose of medication to the syringe by delivering the medication through the uncapped barrel. One exemplary automated device for delivering a prescribed unit dose of medication to the syringe is in the form of an automated device having a fluid delivery device that is movable in at least one direction. The fluid delivery device is adapted to perform the following operations: (1) receiving and discharging diluents from a diluents supply in a prescribed amount to reconstitute the medication in a drug vial; and (2) aspirating and later discharging reconstituted medication from the drug vial into the syringe. The system further includes a sensor for detecting any foreign matter (e.g., undissolved drug, pieces of septum, etc.) present in the reconstituted unit dose of drug prior to transfer of the reconstituted drug (unit dose) to the syringe.

SUMMARY OF THE INVENTION

The present invention relates to a dosage dispenser apparatus configured to be located at patient bedside for measuring and optionally diluting liquid medications and dispensing marked and ready for use syringes filled with the medication.

A dosage dispenser according invention is intended to provide a solution for measuring and dilution of liquid medications and issuing syringes marked and ready for use. The dosage dispenser device carries out actions required for the preparation of a required dose of medication, including identifying medication that is preferably in its standard container; ampoules or vials, breaking them or open the cover, filling a syringe, if needed—diluting the medication in a solution, marking the syringe, disposing of waste and documenting the process, all at the patient bedside with the speed required for critical care. The dosage dispenser is aimed at reducing the number of errors in the dosage, which is a problem, menacing medical services throughout the world. The problem is made acute by considerable pressure on the medical teams while carrying out many and complex procedures under pressure in a situation of uncertainty and with variable data.

Dosage dispenser device according to embodiments of the present invention is designed for medical staff in various medical facilities such as: all wards & outpatient clinics as a resuscitation cart, and in any wards which use other injectable medications such as: Oncology, Intensive Care, Trauma and Resuscitation, Anesthesia and Cardiology.

Dosage dispenser device according to embodiments of the present invention prepares injectable medications and at the same time make available large database on the medications, procedures, drug interactions.

The system can provide a set of doses needed for a procedure such as a resuscitation set of syringes, optionally prepared for a patient with known weight.

Dosage dispenser device according to embodiments of the present invention is portable, it may be maneuvered and stationed at the patient bedside being able to use patient life signs in order to suit the optimal dose to the patient condition.

Main Aspects of the Present Invention are:

Dosage dispenser device according to embodiments of the present invention may work with resuscitation kit designed as magazines that include plurality of kinds and amount of medication and syringes a plurality of sizes that may be needed for one resuscitation procedure.

In other uses such as Oncology, Anesthesia and Cardiology, the Kit may include different medication and syringes correspondingly.

According to an exemplary embodiment of the current invention, there is no need to know how many medication bottles or ampoules were left before starting a procedure, all required medications have been stored packed marked and sealed as a set for the said procedure with the ability to track and to manage the kit by software.

There is no need to load single bottle or ampoule into the system, just to load magazines (medication, saline and syringes).

Dosage dispenser device according to embodiments of the present invention is mobile and may be used near the patient bed. It provide a solution for measuring dosages and dilution of liquid medications, including issuing syringes which are marked and ready for use not in the hospital pharmacy but near the patient bed in real time, it can use hospital database and life sings enabling the system to recommend and dispense the optimal dose according to the patient condition.

Dosage dispenser device according to embodiments of the present invention is configured to handles different types of medication packaging; breaks medication ampoules and open medication bottles. The same dosage dispenser device according to embodiments of the present invention can handle ampoules and bottles. Ampoules need to be broken and then pumped from the top while bottles come with caps that need to be removed and then the medication needs to be pumped from the bottom, when the bottle is up side down using the same apparatus.

Dosage dispenser device according to embodiments of the present invention is configured to handles different types of syringes to get high accuracy.

Dosage dispenser device according to embodiments of the present invention pumps saline and medication directly to the syringe with no need of pipe cleansing between actions.

The saline and medication that was pumped into the syringe is checked and approved for example by using image processing or weighing and database compare.

Some advantages of the current invention may be that the dosage dispenser device according to embodiments of the present invention is configured for working under time pressure such as critical care and resuscitation locations.

The dosage dispenser device according to embodiments of the present invention prepares injectable medications and at the same time handles a large database including information regarding the medications, procedures and drug interactions.

The dosage dispenser device according to embodiments of the present invention uses magazines that are simple to use: loading medications and syringes into the system is simple as loading a video cassette; there is no need to know how much bottles or ampoules are left before starting a procedure, no need to load single bottle or ampoule into the system.

All required medications have been stored packed marked and sealed as a set for the said procedure with the ability to track and to manage the kit by software.

The dosage dispenser device according to embodiments of the present invention provides accurate and fast dosing I.V. medication at the patient bedside in real time.

The dosage dispenser device according to embodiments of the present invention may integrate the patient real time life signs data in order to determine in real time optimal dose for the patient.

The dosage dispenser device according to embodiments of the present invention may use standard medication ampoules and bottles and standard syringes.

The dosage dispenser device according to embodiments of the present invention uses no pipes between the medication packages to syringe. Thus there is no need to clean pipes.

In the dosage dispenser device according to embodiments of the present invention the syringe is labeled and ready to use.

The dosage dispenser device according to embodiments of the present invention uses image processing to validate the accurate amount of saline and medication solution in the syringes and the existence of air bubble.

According to an exemplary embodiment of the invention, an automated dosage dispensing device is provided comprising: a pumping station configured to pump medication into a syringe from both medication bottle and medication ampoule.

In some embodiments, the pumping station is configured to pump medication into a syringe from a medication bottle while said syringe is positioned below said medication bottle.

In some embodiments, the pumping station is configured to pump medication into a syringe from a medication ampoule while said syringe is positioned above said medication ampoule.

In some embodiments, the device further comprising: a medication magazine holding plurality of medication bottles and medication ampoules; and a medication gripper configured to remove at least one of medication bottle or medication ampoule from said medication magazine and load said at least one of medication bottle and medication ampoule into said pumping station.

In some embodiments, the medication gripper is configured brake the neck of said medication ampoule.

In some embodiments, the pumping station is configured to remove the cap of said medication bottle.

In some embodiments, the device further comprising: a syringe magazine holding plurality of syringes; and a syringe gripper configured to remove at least one syringe from said syringe magazine and load said at least syringe into said pumping station.

In some embodiments, each syringe in said syringe magazine is fitted with a hypodermic needle.

In some embodiments, each of said hypodermic needle is covered with a needle cover.

In some embodiments, the syringe gripper, along with spring apparatus, is configured to: remove said needle cover from said needle prior to loading said needle into said pumping station; and to recap said needle with said needle cover after medication pumping is completed.

In some embodiments, the pumping station is configured to rotate about a horizontal axis to position said syringe below said medication bottle.

In some embodiments, the syringe magazine is configured to hold at least two different sizes of syringes.

In some embodiments, the syringes in the syringe magazine are arranged in a two dimensional array; said syringe magazine is configured to move in a first direction; and said syringe gripper is configured to move in a second direction substantially perpendicular to said first direction for accessing said syringes arranged in said two dimensional array.

In some embodiments, the medication pumping is performed directly through said hypodermic needle.

In some embodiments, the device further comprising a saline magazine configured to hold a saline bag.

In some embodiments, the saline bag is standard intravenous saline infusion bag.

In some embodiments, the saline bag is standard plurality of medication bottles and medication ampoules are standard medication bottles and standard medication ampoules.

In some embodiments, the medication magazine is selected from a group of medication magazine types, wherein each type of said medication magazine types is loaded with medication needed for treating a different medical condition.

In some embodiments, each of said medication magazine is fitted with an RFID device.

In some embodiments, the medication magazine is replaced after each medical procedure. Alternatively, same magazine may be used for a plurality of procedures.

In some embodiments, the device is configured to be placed at patient bedside.

In some embodiments, the device further comprising at least one patient life-sign monitor.

In some embodiments, the patient life-sign monitor is selected from the group comprising: ECG monitor, EEG monitor; blood oxygen monitor; patient temperature monitor; and blood pressure monitor.

In some embodiments, the device is further comprising a computer analyzing signals from said at least one patient life-sign monitor and recommending medication based on said signal analysis.

In some embodiments, the device is further comprising a computer recommending medication based on patient information and user input regarding patient medical condition.

In some embodiments, the recommending medication based on said signal analysis is further based on patient information.

In some embodiments, the patient information is selected from a group comprising: patient weight; patient age; patient gender; patient known allergies; and other medications used by said patient.

In some embodiments, the syringe magazine is configured to hold said syringes in a predetermined orientation.

In some embodiments, the device is further comprising a medication camera verifying at least one of: medication type; medication lot number; medication expiration date; and amount of medication in the medication container.

In some embodiments, the device is further comprising a syringe camera verifying at least one of: amount of medication pumped into said syringe; absence of air bubbles in said syringe. The vision system may be capable to capture and process plurality of syringe sizes, for example at least 4 sizes of syringes.

In some embodiments, the medication volume measured by the camera is calibrated.

In some embodiments, the device is configured to be mobile and be moved to patient bedside.

In some embodiments, the device further comprises wheels to ease moving said device to patient bedside.

In some embodiments, the time from ordering medication to dispensing a syringe with the required medication is less than 60 seconds.

In some embodiments, the time from ordering medication to dispensing a syringe with the required medication is less than 30 seconds.

In some embodiments, the time from ordering medication to dispensing a syringe with the required medication is less than 20 seconds.

According to another embodiment, of the current invention, a method of dispensing syringe with medication is provided comprising the steps of: loading a pumping station with any one of: medication bottle or medication ampoule; loading a syringe fitted with hypodermic needle into said pumping station; pumping medication from said one of medication bottle or medication ampoule into said syringe through said hypodermic needle; and dispensing said syringe.

In some embodiments, the said pumping medication into a syringe from a medication bottle is performed while said syringe is positioned below said medication bottle.

In some embodiments, the pumping medication into a syringe from a medication ampoule is performed while said syringe is positioned above said medication ampoule.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the Drawings:

FIG. 3a schematically depicts a standard medication bottle as used in the system acceding to the current invention.

FIG. 3b schematically medication depicts a medication gripper 20 holding a medication bottle 35 acceding to the current invention.

FIG. 3c schematically depicts a camera 4 for medication check and control acceding to an exemplary embodiment of the current invention.

DESCRIPTION OF THE PREFERRED EMBODIMENTS

Figure 1A:
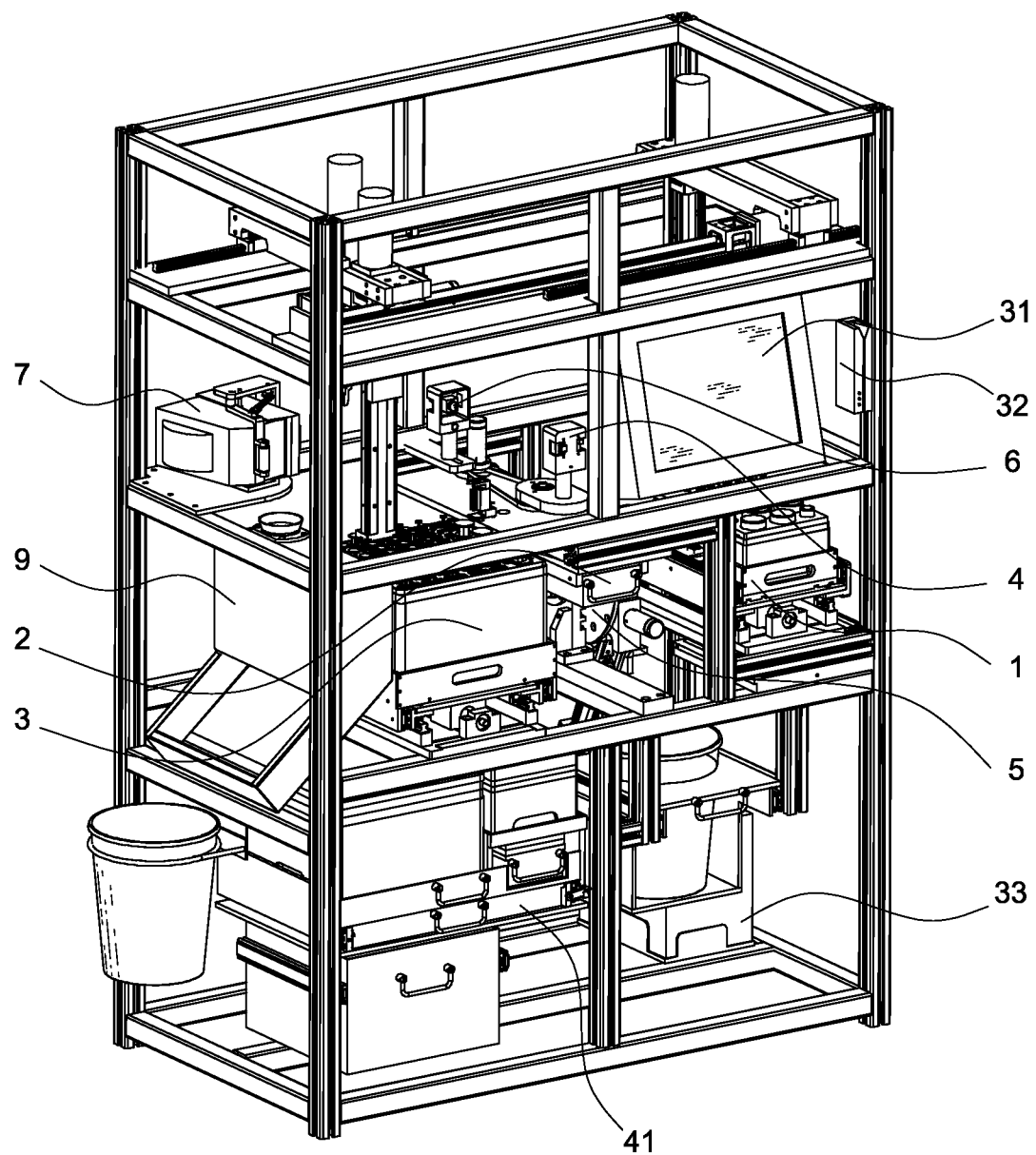
FIG. 1a schematically depicts a dose dispenser seen without its covers according to an exemplary embodiment of the current invention.

The present invention relates to a dosage dispenser apparatus configured to be located at patient bedside for measuring and optionally diluting liquid medications and dispensing syringes filled, marked and ready for use.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts.

The drawings may not be to scale. For clarity, non-essential elements were omitted from some of the drawings.

FIG. 1a schematically depicts a dose dispenser seen without its covers according to an exemplary embodiment of the current invention.

Dose dispenser 100 comprises a main frame 151 supporting its components including: Medication Magazine 1; Saline magazine 2; Syringes magazine 3; Camera for medication check and control 4; Pumping carousel 5; Syringe Camera 6 for syringe volume check; Syringe label printing and sticking unit 7; Needle cover handling unit 219; Syringe dispensing apparatus 9 having Syringe submission tray 99; Sharps waste disposal container 10; medication gripper 20; Syringe gripper 141; Touch Screen 31; Card Reader 32; waste disposal container 44; Keyboard with pointing device 102; computer 33; and an optional backup battery such as Uninterrupted Power Supply (UPS, not seen in this figure).

Some components marked in this figure are detailed later.

Figure 1B:
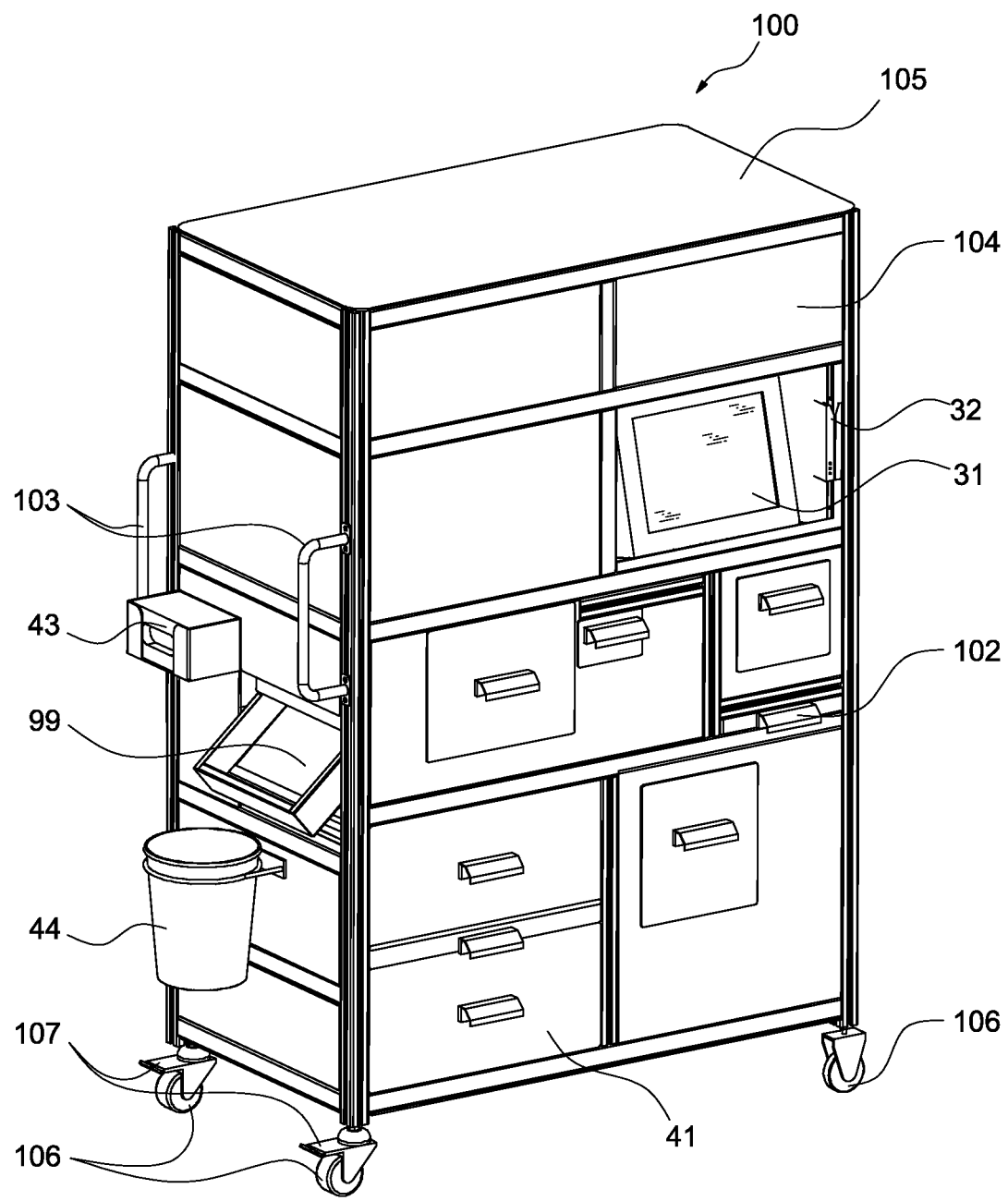
FIG. 1b schematically depicts a dose dispenser seen with its covers according to an exemplary embodiment of the current invention.

FIG. 1b schematically depicts a dose dispenser seen with its covers according to an exemplary embodiment of the current invention.

Dose dispenser 100 seen in FIG. 1b showing: a main frame 151; side covers 104; top cover 105 which may be used as work space; optional handles 103 which may be used for transporting the dispenser by rolling it on its wheels 106 at least two of which are preferably equipped with stoppers 107.

Also seen in FIG. 1b are: Touch Screen 31; Card Reader 32; Syringe submission tray 99; waste disposal container 44; Keyboard with pointing device 102 (seen here in retracted position); gloves box 43; and drawers 41 and 333, for storing of other devices and machines that are in use throughout resuscitation, for example apparatus such as defibrillator, Ambo bagging, airways, Ambo resuscitator, knives, etc. In some embodiments, drawers 41 and 333 hold a sensor or sensors such as ECK; EEG; thermometers; oximeter for acquiring data concerning the patient health. In some embodiments, computer 33 analyze the patient condition, optionally issue an alert when condition changed or become critical and optionally suggest medication to be administered and optionally prepare the suggested medication. Optionally, additionally or alternatively, drawers may store replacement magazines, for example medication magazines for use with different patient, for different procedure or if on or few of the supplies in a magazine used by the dispenser is finished or at low level.

Preferably, dosage dispenser 100, according to embodiments of the present invention, is placed in locations where emergency medical care is provided, for example in hospital emergency room, intensive care units, ambulances, etc.

The dosage dispenser dispense a "ready for injection" syringe, already filled with the correct amount of medication, on demand received trough at least one of its input devices touch screen 31, keyboard and pointing device 102.

The necessary medications are stored within dosage dispenser 100 in medication magazine 1. Proper amount of medication or combination of a plurality of medications is loaded into a syringe of proper size, already fitted with hypodermic needle, selected from a collection of syringes stored in syringes magazine 3. Optionally, the medication is diluted in proper amount of saline drawn from a saline bag housed in saline magazine 2.

The syringe is labeled with a proper label specifically printed by the syringe label printing and sticking unit 7. The syringe is than dispensed through syringe dispensing apparatus 9 onto syringe submission tray 99.

Dosage dispenser 100, according to embodiments of the present invention, is configured to work with resuscitation kit designed as magazines that includes all kind and amount of medication that are needed for one resuscitation procedure.

There is no need to know how much bottles/ampoule lefts before starting a procedure, no need to load single bottle/Ampoule into the system, just load magazines, (medication, saline and syringes)

Dosage dispenser device according to embodiments of the present invention is mobile. It can be moved using optional handles 103 and wheels 106 and can be used near the patient bed. Preferably, wheels are locked using optional locks 107 before use. Optional UPS backup power supply optionally maintains computer operation and optionally other processes while the dose dispenser is disconnected from power while it is moved. However, mechanical motion may optionally be halted while the system is being moved to prevent accidental dropping of medication or syringes due to vibrations.

The device provides a solution for measuring dosages and dilution of liquid medications, including issuing syringes which are marked and ready for use not in the hospital pharmacy but near the patient bed in real time and can use life sings enabling the system to recommend and dispense the optimal dose according to the patient condition.

Dosage dispenser device according to embodiments of the present invention is a computer based system that works under mechanical and electronics control. The system may replaces the resuscitation cart that is in use today in many departments in hospitals, to be used in situations such as resuscitation, pulmonary edema, tachycardia bradycardia, fibrillation, etc.

Dosage dispenser device according to embodiments of the present invention automates the preparation of liquid medication: Determines dosage, dilutes and draws syringe. Preferably, the device is easy to use as it includes all information needed in one place, colored and detailed. Dosage dispenser device according to embodiments of the present invention is preferably fully controlled throughout all the medication dispensing process and displays status and warning signals on screen 31 and optional LEDs warnings preferably installed near display 31 (LEDs are not seen in this figure).

To activate the system, the operator (typically a doctor or medical personnel) sweeps his/her employee card on the card reader 32 to get approval for using the system. Alternatively, password may be entered using keyboard 102 or the virtual keyboard on the touch screen 31. Optionally, the system may be used for accessing data base information. In this case, access may be granted to people not authorized to activate medication dispensing activity. Optionally the computer recognize the authorization level of the user, for example by using a password, a code on the card or a combination and grant the user the ability to perform specific tasks appropriate to that specific user. For example, a technician may be authorized to re-program the computer or to change data sets; a doctor may be authorized to view patient's records and issue medication; and a nurse may be ale to only view records.

To start dispensing medication the operator preferably input a request. The request may be in the form of specifically requesting type and amount of medication. Alternatively or additionally, the operator may input the nature of the patent condition or the procedure to be done on the patient and optionally some details of the patient and the computer within the dispenser uses database to select medication or medication mix and optionally calculate the recommended amount. Patient details may be obtained from patients' records, for example at hospital data base.

The operator optionally inputs the patient weight category and risk category. Weight categories can be categorized, for example in the following groups: 1-60 Kg, 61-90 Kg, 91-150 Kg, 151-250 Kg, 250 Kg and up. Additionally, weight adjustment for the 1-60 Kg group can be for example in groups like: 3 Kg, 4 Kg, 5 Kg, 6-7 Kg, 8-9 Kg, 10-11 Kg, 12-14 Kg, 15-18 Kg, 19-22 Kg, 24-28 Kg, 30-36 Kg, 37-60 Kg. Alternatively, exact or estimates weight (in Kg or lb may be entered. Preferably, this information is retained and used for the same patient throughout the treatment.

Risk Categories may include Kidney Disease, Liver Disease, Age over 80 years old; known allergies; etc.

The operator optionally selects the procedure and a default dosage for every drug is shown on the display screen regarding the selections done. Optionally, the operator may override default dosage displayed. If the amount of the requested medication is above the amount that is allowed to give to the patient, a warning is displayed informing the user the amount that can be issued to this patient exceeds (more than that will harm the patient). Optionally if the procedure goes for a long time and the amount that was asked for the patient is grater than the amount stored in the medication magazine a warning is displayed informing the user the amount that can be issued is finished and the amount that need to be obtained from another source. With the optional user's approving the suggested selection, medication preparation starts.

Supplies for the system are stored in three dedicated magazines: medication magazine 1; saline magazine 2; and syringe magazine 3.

Figure 2A:
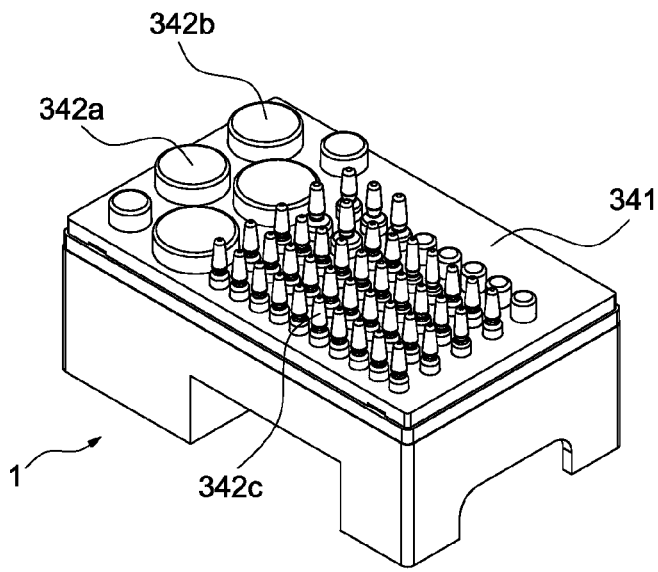
FIG. 2a schematically depicts medication magazine 1 which can be inserted into the system 100 according to the exemplary embodiment of the current invention.

FIG. 2a schematically depicts medication magazine 1 which can be inserted into the system 100 according to the exemplary embodiment of the current invention.

Medication magazine 1 comprises a tray 341 with receptacles, preferably configured to hold several types of medication containers, such as bottles and ampoules of different sizes. For clarity, only few of which are labeled (342a, 342b and 342c). It should be noted that different types of medication magazine 1 may be used, having different size of receptacles for medication containers and containing different types and amounts of medications depending on the medical applications.

Each receptacle preferably configured to snugly fit the medication container that assigned to it. Preferably, each receptacle holds only one type of medication; however, few receptacles may hold the same medication as same type of medication may be administered more than once during a medical procedure.

Preferably, the quantity for each drug in medication containers inserted in the receptacles in the magazines may be same as the quantity used today in typical resuscitation (or other) kits in the hospitals. Preferably standard medication containers are used. Preferably, standard medication ampoules, vile or bottles are used. The use of standard medication container leads to flexibility and reduce cost of the medication and the ability to switch from one medication provider to another. The location, type, concentration and amount of medication in each medication receptacle in medication tray 341 is stored in the computer's data base so that the correct medication container may be retrieved and correct amount drawn.

Preferably, medication vials are stored at its designated place upside down. This orientation eases gripping the medication containers by the gripper (seen in the following figures).

Figure 2B:
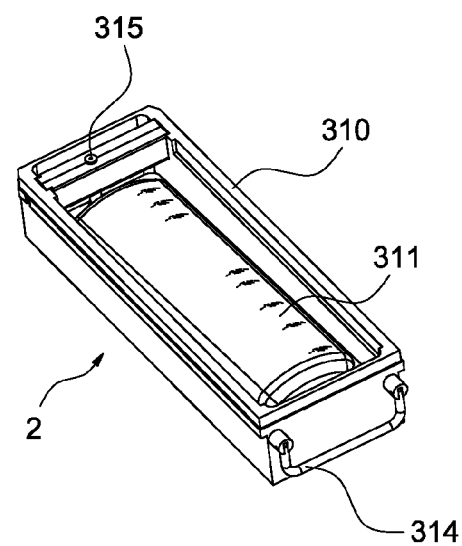
FIG. 2b schematically depicts the saline magazine 2 which can be inserted into the system 100 according to the exemplary embodiment of the current invention.

FIG. 2b schematically depicts the saline magazine 2 which can be inserted into the system 100 according to the exemplary embodiment of the current invention.

Saline magazine 2 comprises a saline drawer 310 holding a bag of Saline 311. Saline is drawn from the bag by piercing silicon pipe 315 that comes with the bag. Saline is used for diluting the medication when needed. Handles 314 eases placing and removing saline magazine 2.

An amount of saline or medication pumped is controlled by the length of motion of plunger pincher 18 on gripper 141. The motion is controlled by computer 33 using a servo motors or a step motor.

Figure 2C:
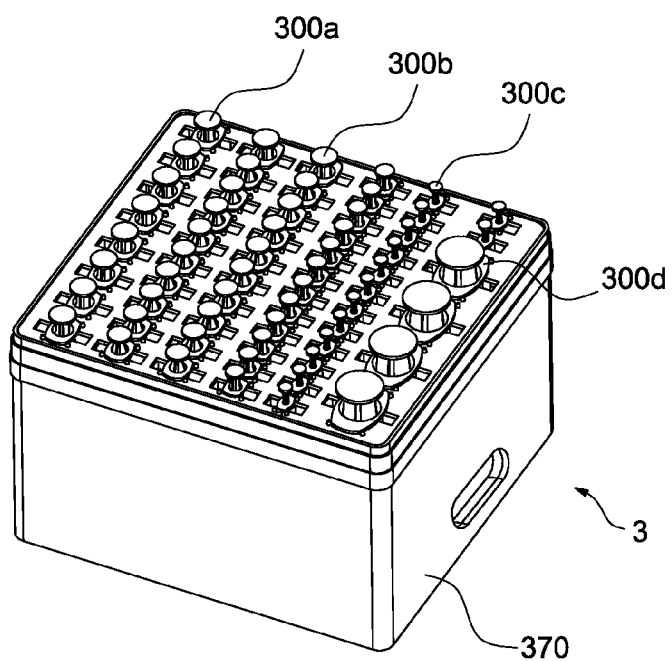
FIG. 2c schematically depicts the syringe magazine 3 which can be inserted into the system 100 according to the exemplary embodiment of the current invention.

FIG. 2c schematically depicts the syringe magazine 3 which can be inserted into the system 100 according to the exemplary embodiment of the current invention.

Syringe Magazine 3 comprises a syringe tray 370 with a plurality of syringe receptacles for syringes of different volumes 300a, 300b, 300c and 300d (for example: 1 cc, 2.5 cc, 5 cc, 10 cc and 50 cc). Four types of syringes are seen in this figure; however number and types of syringes may vary. The syringes are placed in the magazine 3. Preferably, syringes are all placed in tray 370 in same orientations so that all scale marks directed to the same side. This may ease later disclosed image processing without the interfering of the scale mark. It is also easy to put a label to mark the syringe without covering the scale mark, so that the doctor can still see and read the dosage amount that in the syringe.

According to an embodiment of the invention, medication magazine need to be replaced after each procedure. In some embodiments, once a procedure ends, the system needs re-activation by changing at least the medication magazine and preferably all of medication, saline and syringe magazines.

Reactivation may be performed by an RFID tag affixed to the magazines or a barcode on the magazines or an authorization code that is entered using the keyboard or a magnetic card that placed in the package of a replacement magazine and is read by the card reader.

FIG. 3a schematically depicts a standard medication bottle as used in the system acceding to the current invention.

The system preferably uses standard bottles and ampoules. Bottles 35 come with caps 37 that need to be taken off before the silicon head 36 can be stabbed with the syringe's hypodermic needle and medication may be drawn.

FIG. 3b schematically medication depicts a medication gripper 20 holding a medication bottle 35 acceding to the current invention.

Each ampoule or vial of medication is stored in away which enable the gripper 20 to pull the required medication out of medication magazine 1.

Medication gripper 20 is equipped with movable jaws 211 and can move up and down (z axis) on vertical rail 212. Grabbing is actuated by closing the jaws 211 using motor 101a.

Motion along Z axis on rail 212 is actuated by motor 101b. Additionally, as can be seen in FIG. 1a, medication gripper 20 can move horizontally left and right (X axis) on horizontal rails 207 using motor 101b. To access all the receptacles in medication magazine 1, the medication magazine 1 is placed on a horizontal rail 119 (seen in FIG. 1a) which enables controlled motorized motion in the front to back (y axis).

FIG. 3c schematically depicts a camera 4 for medication check and control acceding to an exemplary embodiment of the current invention.

In FIG. 3c, medication gripper 20 is seen holding a medication container such as medication bottle 35 in front of camera for medication check and control 4. Camera for medication check and control 4 is situated on camera rotation stage 218. Motor 101d rotates the camera rotation stage 218 using belt 216. By rotating camera 4, medication container may be inspected from several angles. Using image processing software such as Optical Character Recognition (OCR), the computer may optionally read the medication label and verify that the correct medication container was used. Optionally, barcode may be printed or affixed to the medication container and used for medication recognition. If a barcode is used, a barcode reader may replace camera 4. Optionally, an image or several images of medication container may be kept as a record.

Figure 4:
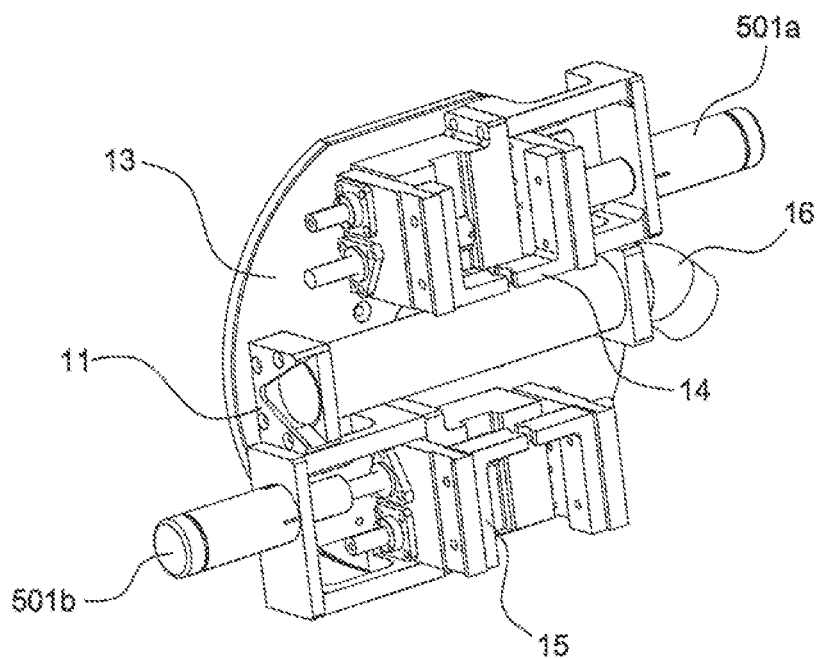
FIG. 4 schematically depicts the pumping carousel 5 according to an exemplary embodiment of the invention.

FIG. 4 schematically depicts the pumping carousel 5 according to an exemplary embodiment of the invention.

Pumping caroused 5 comprises a pumping turning plate 13 which can rotate using a motor 503 (seen in FIG. 6).

Figure 9:
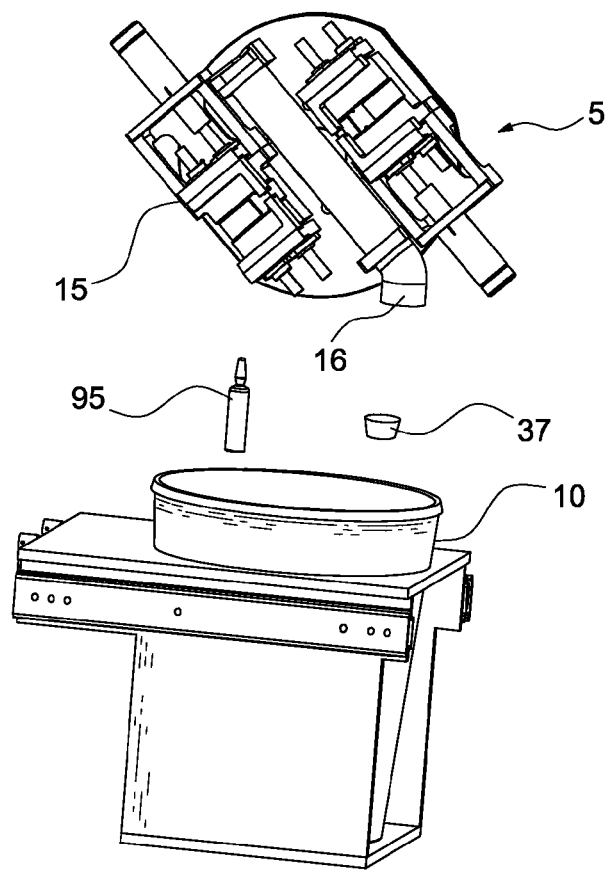
FIG. 9 schematically depicts disposal of opened ampoule 95 and bottle cap 37 from carousel 5 into waste disposal container 10 according to an exemplary embodiment of the invention.

One function of pumping carousel 5 is to remove the cap 37 covering the silicon head 36 of medication bottle 35. To remove the cap, caroused 5 is rotated so bottle cover remover 11 is on the top. Bottle cover remover unit 11 engages the cap 37 while bottle 35 is held by medication gripper 20, and the bottle is pulled up by a vertical upward movement of the gripper 20 thus braking and removing the cap. The caps come off exposing the silicon head 36. The cap 37 then falls down through pipe 16 to the internal sharps waste disposal container 10 (as seen in FIG. 9). After cap removal, the bottle 35 is transferred and held by the medication Bottle/Ampoule holder 14 installed on pumping turning plate 13 of pumping carousel 5.

Figure 5A:
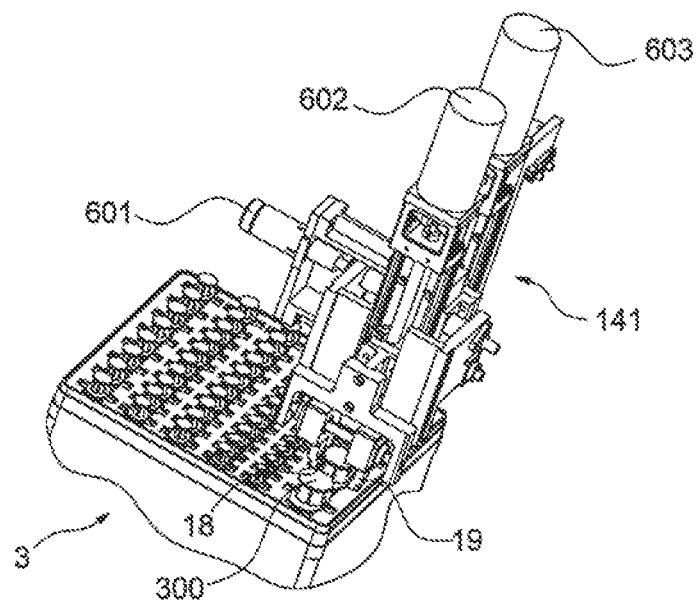
FIGS. 5a and 5b schematically depict syringe gripper 141 removing a syringe 300 from syringe magazine 3 according to an exemplary embodiment of the invention.
Figure 5B:
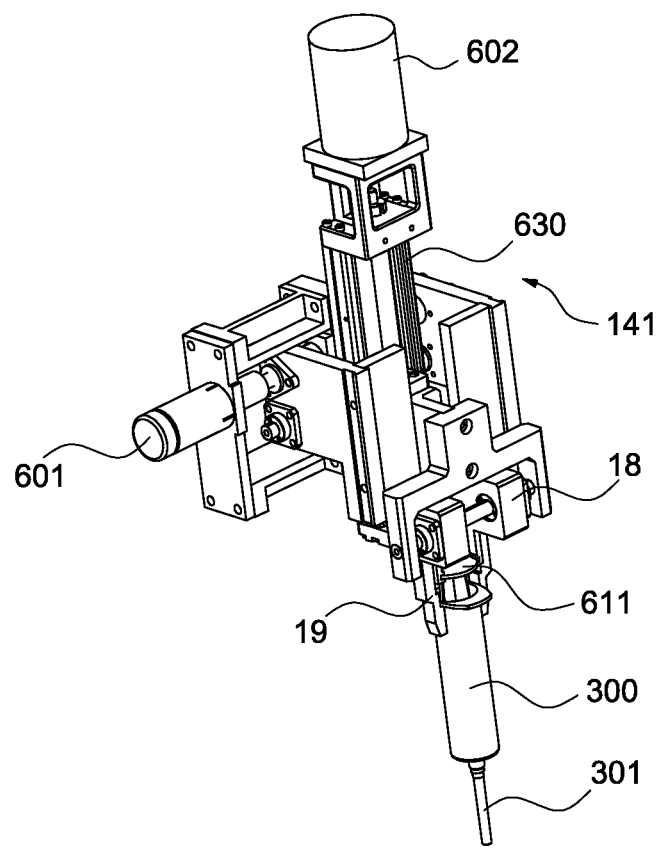

FIGS. 5a and 5b schematically depict syringe gripper 141 removing a syringe 300 from syringe magazine 3 according to an exemplary embodiment of the invention.

Syringe gripper 141 comprises two pincers: syringe body pincher 19 for holding the syringe 300; and plunger pincher 18 for holding the plunger 611 during pumping liquid. Syringe gripper 141 is positioned above the required syringe 300, pincers 18 and 19 are open and gripper 141 is lowered to position. Pincers 18 and 19 are closed and hold the syringe body 300 and the syringes plunger 611. The two grippers open and close together. Motor 602 moves the inside plunger pincer 18 separately to pull the plunger upward for liquid pumping.

Syringe gripper 141 moves up and down (z axis) on vertical rail 630 by motor 602. Syringe gripper 141 moves horizontally from right to left (x axis) on horizontal rails 207 (seen in FIG. 1a) by motor 603 (seen on FIG. 1a) (omitted for clarity from FIG. 5b). To access all the syringes in syringe magazine 3, the syringe magazine 3 is placed on a horizontal rail 118 (seen in FIG. 1a) which enables controlled motorized motion in the front to back (y axis). Syringe 300 is fitted with a hypodermic needle, seen in FIG. 5b covered with needle cover 301.

Figure 6A:
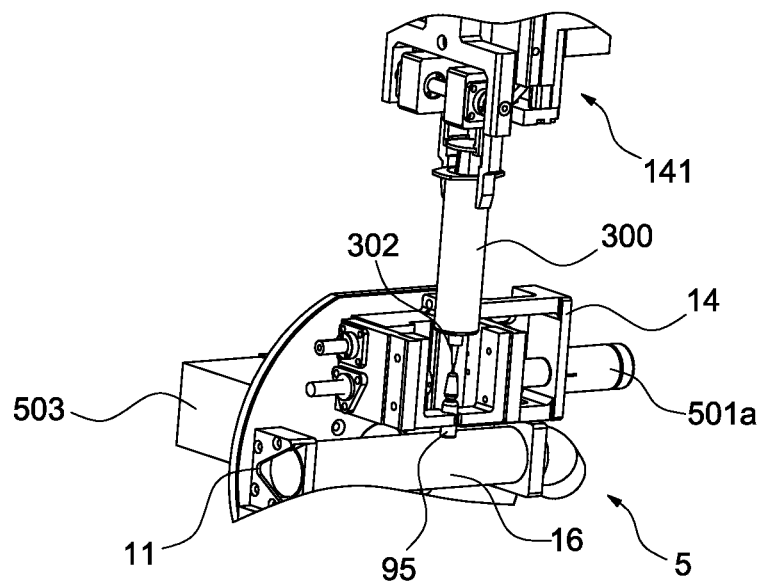
FIGS. 6a schematically depicts syringe gripper 141 holding syringe 300 and pumping through needle 302 medication from ampoule 95 held in medication holder 14 located on carousel 5 according to an exemplary embodiment of the invention.

FIG. 6a schematically depicts syringe gripper 141 holding syringe 300 and pumping through needle 302 medication from ampoule 95 held in medication holder 14 located on carousel 5 according to an exemplary embodiment of the invention.

Before medication can be pumped out, the syringe is lowered by syringe gripper 141 to the needle cover remover 219 (seen in FIG. 3b). The needle cover 301 is removed using a spring that holds the needle cover 301 without bending or breaking needle 302. While the needle cover 301 is held in cover remover 219, the syringe moves up and the needle 302 is revealed.

If needed, the saline, a dilution solution, is first to be pumped into the syringe so that it is not contaminated with medications. The same bag is used throughout all the resuscitation (or other) procedure, and may be used more than once. The syringe is lowered by syringe gripper 141 to the saline magazine 2 so that needle 302 pierces the bag's pumping location 315 (Seen in FIG. 2b). Syringe body pincher 19 holds the syringe 300; and plunger pincher 18 pulls plunger 611 upwards for pumping saline.

Optionally, once the saline has been drown into the syringe, syringe gripper 141 places the syringe 300 in front of syringe camera 6. Syringe camera 6 acquires image or plurality of images of the syringe and the computer 33 determines by image whether the right amount of saline has been drawn into the syringe to ensure correct amount of dilution.

Both medication and syringe are now moved to a pumping carousel 5. Medication is moved by medication gripper 20 and syringe by syringe gripper 141.

The pumping carousel is designated to draw medication from a bottle when is to be held upside down and from ampoules to be held facing up.

On the carousel there are two holders: medication holder 14; and syringe holder 15. Medication holder 14 holds the medication (ampoule 95 or bottle 35). Syringe holder 15 is adopted to hold the syringe 300.

When the needed medication is in an ampoule, the ampoules neck needs to be broken to allow access to the medication. Ampoule 95 is removed by medication gripper 20 and is placed in medication Bottle/Ampoule holder 14. The medication gripper 20, still holding the ampoule head is moved and the head of ampoule 95 breaks. Medication gripper 20 than release the broken head of ampoule 95 into the disposal container 10.

For pumping medication from an ampoule 95, medication gripper 20 inserts the ampoule 95 into medication holder 14. It is than moved to brakes open the ampoule. Syringe gripper 141 moves syringe 300 such that needle 302 is deep in the liquid medication in the ampoule. Syringe body pincher 19 holds the syringe 300; and plunger pincher 18 pulls plunger 611 upwards for pumping medication out of the ampoule 95.

For pumping medication from a bottle 35, medication gripper 20 inserts the bottle 35 into medication holder 14. Carousel 5 is than rotated by 180 degrees so that the bottle 35 is positioned with exposed silicon head 36 facing up.

Syringe gripper 141 moves syringe 300 such that needle 302 pierces silicon head 36 and is deep in the liquid medication in the bottle.

The syringe 300 is held with the syringe holder 15 on the Carousel, the syringe gripper 141 is then open the pinchers 18 and 19. The Carousel 5 is than rotate for pumping the bottle in an upside down position.

Figure 6B:
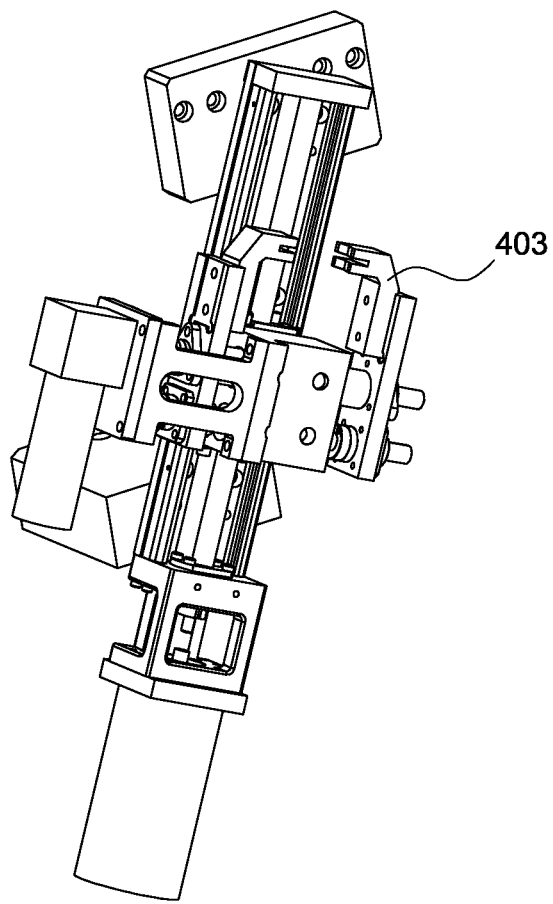
FIG. 6b schematically depicts a lower plunger gripper 40 according to an exemplary embodiment of the current invention.

FIG. 6b schematically depicts a lower plunger gripper 40, according to an exemplary embodiment of the current invention.

Lower plunger gripper 40 comprises plunger pincher 403 which can be closed by motor 401a and hold the syringe plunger.

Plunger pincher 403 can than be moved down on vertical rail 402 by motor 401b and pull plunger 611 downwards for pumping medication out of the bottle.

After pumping is completed, plunger pincher 403 is than opened, releasing the plunger, and carousel 5 rotates back so that the syringe is on top and can be grabbed by syringe gripper 141. Optionally, used medication bottle is released and fall into waste disposal container 10 by opening medication holder 14. Alternatively, medication bottle 35 not empty, and the medication in it may be needed again, bottle 35 may be returned by medication gripper 20 into its receptacle in medication magazine 1.

Optionally, once the medication has been drown into the syringe, syringe gripper 141 places the syringe 300 in front of syringe camera 6. Syringe camera 6 acquires image or plurality of images of the syringe and the computer 33 determines by image processing whether the right amount of medication (or mixture of saline and medication) has been drawn into the syringe to ensure correct amount of dilution. Additionally and optionally, images acquired by syringe camera 6 are used for verification that no bubbles are trapped in the syringe. Additionally and optionally, images acquired by syringe camera 6 are used for verification that needle 302 is not bent or missing.

Figure 7:
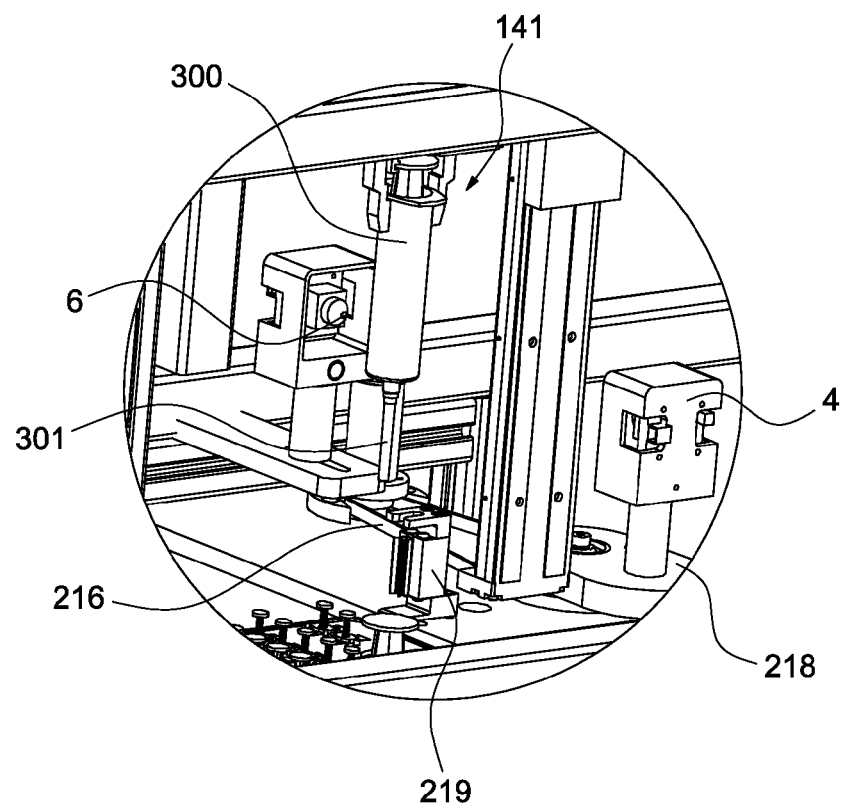
FIG. 7 schematically depicts the syringe gripper 141 near cameras 4 and 6 after the needle 302 was covered again by needle cover 301 using needle cover remover 219 according to an exemplary embodiment of the invention.

FIG. 7 schematically depicts the syringe gripper 141 near cameras 4 and 6 after the needle 302 was covered again by needle cover 301 using needle cover remover 219 according to an exemplary embodiment of the invention.

When the syringe has passed all the preparation and has been inspected and approved, the needle cover is assembled back. The syringe is lowered by syringe gripper 141 to the needle cover remover 219 (seen in FIG. 3b). The syringe gripper 141 is then moves on the x axis to release the needle cover 301 from the spring that holds it and needle 302 is covered.

Figure 8:
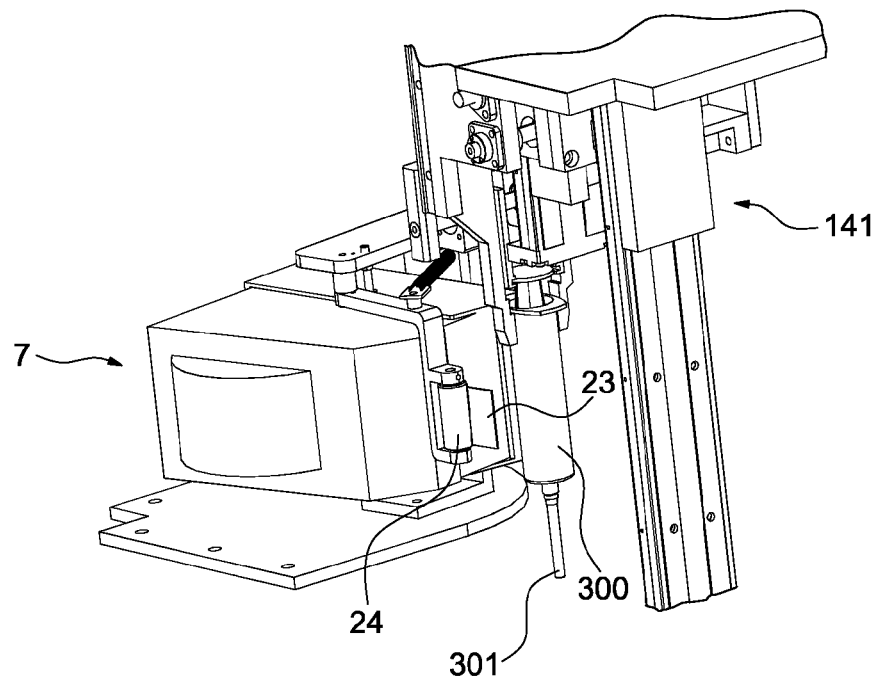
FIG. 8 schematically depicts syringe label printing and sticking unit 7 ready to affix label 23 on syringe 300 according to an exemplary embodiment of the invention.

FIG. 8 schematically depicts syringe label printing and sticking unit 7 ready to affix label 23 on syringe 300 according to an exemplary embodiment of the invention.

After filling the syringe and re-installing the needle cover, the syringe is now labeled with a label preferably noting information such as: type and amount of medication (and optional dilution); date and/or time of medication preparation; Expiration date of the medication (if applicable); name of patient; name of the doctor ordering the medication; billing information; procedure done to the patient; notes and warnings related to the medication or the patient; typed text or barcode or both, etc.

Syringe label printing and sticking unit 7 prepares a label 23 having adhesive on one side and places it pulled out aligned with a roller 24, when the syringe moved by syringe gripper 141 against the roller which applies the label on the syringe 300.

FIG. 9 schematically depicts disposal of opened ampoule 95 and bottle cap 37 from carousel 5 into waste disposal container 10 according to an exemplary embodiment of the invention.

Waste disposal container 10 is preferably used for all the leftover medication containers used during the operation of dispenser 100.

For example, after medication gripper 20 brakes off the neck of ampoule 95, it releases the broken neck into waste disposal container 10.

Additionally and optionally, after the cap 37 is removed from bottle 35 by bottle cover remover 11, cap 37 goes through pipe 16 into waste disposal container 10.

Additionally and optionally, after medication is pumped from ampoule 95, medication holder 15 may release the ampoule, as depicted in FIG. 9, dropping ampoule 95 into waste disposal container 10.

After medication is pumped from medication bottle 35, carousel 5 rotates so that medication bottle 35 is in the upper side. Medication gripper 20 is positioned and holds the bottle, medication holder 14 releases the bottle which is removed from the carousel 5. Additionally and optionally, medication bottle 35 may be returned by medication gripper 20 to its original receptacle in medication magazine 1, or preferably it may be dropped by medication gripper 20 into waste disposal container 10.

Figure 10:
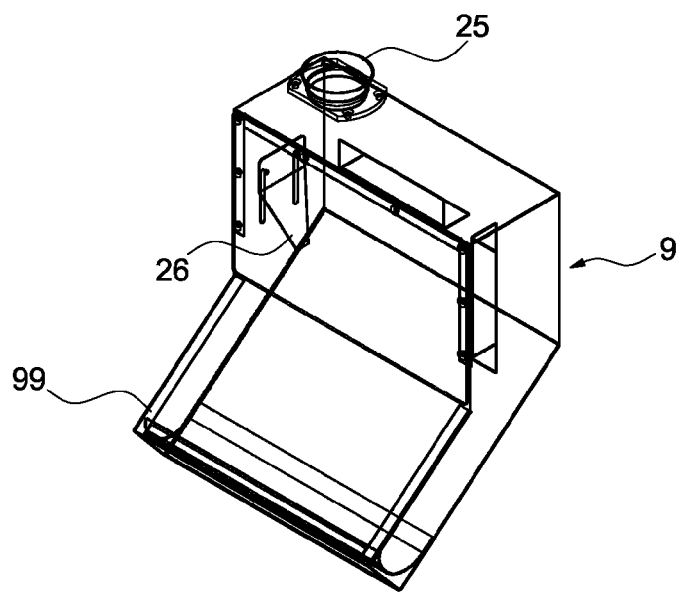
FIG. 10 schematically depicts syringe dispensing apparatus 9 having syringe entrance cone 25, a syringe director lip 26 and syringe tray 99 according to an exemplary embodiment of the current invention.

FIG. 10 schematically depicts syringe dispensing apparatus 9 having syringe entrance cone 25, a syringe director lip 26 and syringe tray 99.

The syringe loaded with the medication, approved and labelled, is released by syringe gripper 141 through syringe entrance cone 25, into syringe dispensing apparatus 9 that is designed to receive the syringe at the cone 25 so that the syringe is directed by director lip 26 to lay horizontal on syringe tray 99 in a way that enables the syringe to be placed on a slope beside other syringes that had been already issued.

Computer 33 optionally collects and stores information during the operation of dose dispenser 100. For example all medical information that was collected through the medical procedure (e.g. resuscitation; pulmonary edema; tachycardia; or bradycardia process) for example by external medical sensors such as ECK; EEG; thermometer; blood pressure monitor; pulse oximeter; or entered by the user, may be saved in the computer database; preferably with associated time stamp, and may be available to the user, for example, using CD; Disk On Key; or other communication links such as LAN or preferably wireless communication. The information may include: Patient details; Doctor details; Medications details (Including Name, dosage, dilution, manufacture, Lot number); Other Procedure details.

Figure 11:
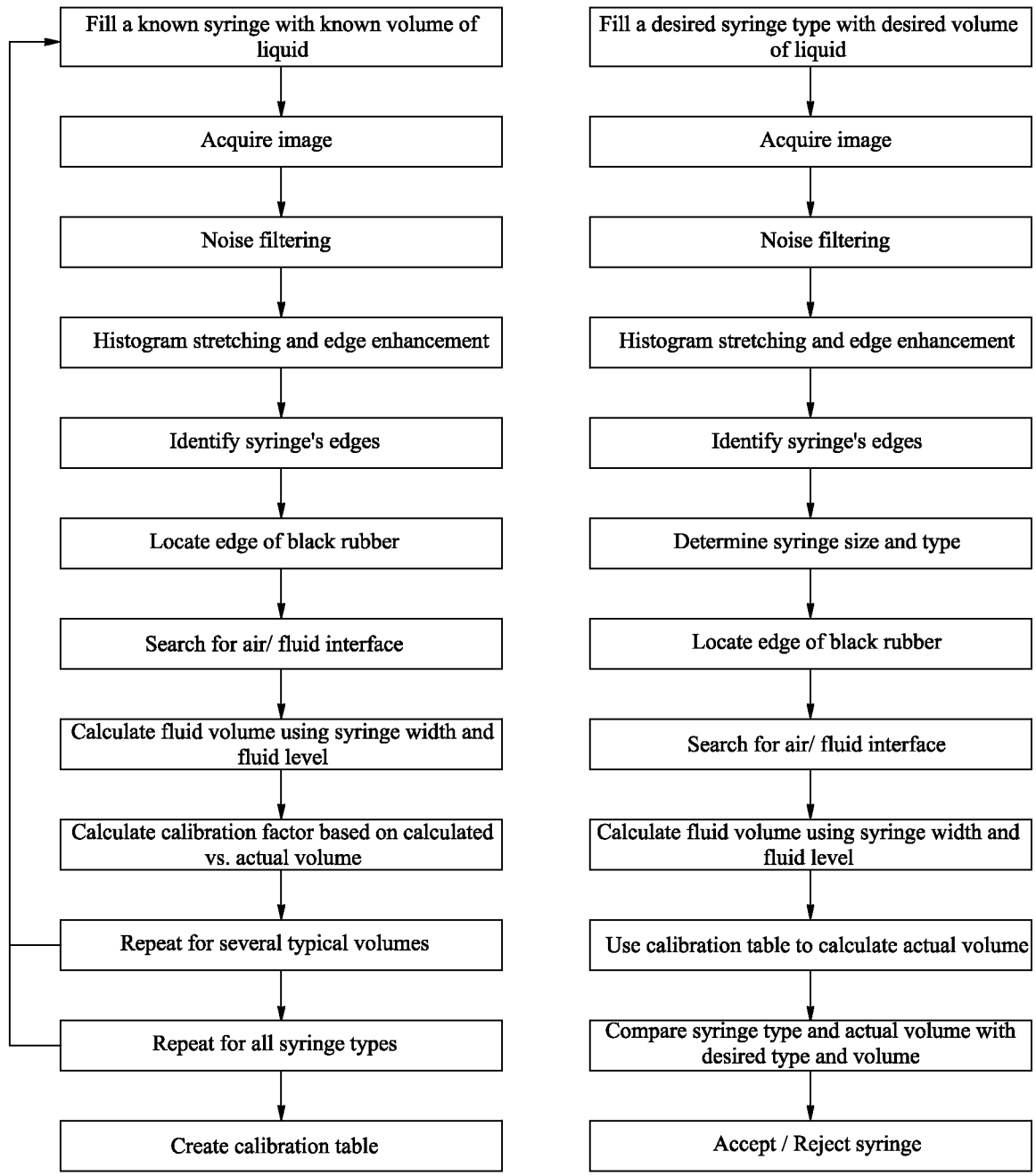
FIG. 11 schematically depicts a method of syringe volume measurement and calibration using vision subunit according to an exemplary embodiment of the current invention.

FIG. 11 schematically depicts a method of syringe volume measurement and calibration using vision subunit according to an exemplary embodiment of the current invention.

According to the depicted exemplary embodiment, the camera is preferably positioned in 90 degree to the syringe so that the long side of the camera's image rectangle is matching the length of the syringe and not the syringe width.

First, a calibration procedure is done, preferably at manufacturing, and optionally during service. Preferably calibration is done for each system.

The calibration process results in creation (or updating during service) a calibration table used for correcting calculated measured liquid volume in a syringe to actual volume in the syringe due to optical distortions and other variations such as actual camera-syringe distance; etc.

The calibration process comprises of the following steps:
A. System Calibration

Fill a known syringe with known volume of liquid (Type of syringe and volume of liquid are preferably verified by the operator).

Acquire image

Noise filtering

Histogram stretching and edge enhancement

Identify syringe's edges

Locate edge of black rubber

Locate air/fluid interface

Calculate (measured) fluid volume using syringe width and fluid level (wherein fluid level is the distance between the upper edge of the plunger's black rubber stopper and the air/liquid interface)

Calculate calibration factor based on calculated (measured) vs. actual (known) volume Repeat (steps 1-9) for several typical volumes Repeat (steps 1-10) for all syringe types Create calibration table During regular use, the system verifies that the syringe of the desired type was indeed filed with the desired volume of liquid medication. The verification preferably comprises the following steps:
B. Syringe Verification Fill a desired syringe with desired volume of liquid.

Acquire image

Noise filtering

Histogram stretching and edge enhancement

Identify syringe's edges

Determine syringe size and type (if the type of syringe is not the desired type, syringe may be rejected and process terminates with error message to the user)

Locate edge of black rubber

Locate air/fluid interface

Calculate (measured) fluid volume using syringe width and fluid level (wherein fluid level is the distance between the upper edge of the plunger's black rubber stopper and the air/liquid interface)

Use calibration table to calculate actual (calibrated) volume (based on measured volume, syringe type and calibration table. In some cases, interpolation between two calibration values may be used)

Compare syringe type and actual volume with desired type and volume

Accept/Reject syringe (if the determined syringe type is not the desired type or if the actual volume is outside tolerance range from the desired volume—syringe may be rejected and process terminates with error message to the user)

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An on demand dosage dispensing device configured to be located at patient bedside comprising:

a medication magazine adapted to hold a plurality of standard medication containers;

a syringe magazine adapted to hold a plurality of syringes having varying sizes, wherein each of the plurality of syringes is fitted with a hypodermic needle and each hypodermic needle is covered with a needle cover;

a pumping carousel configured to have medication drawn through the needle of at least one selected syringe, selected from said plurality of syringes, wherein the pumping carousel is configured to draw the medication from a bottle while the selected syringe is positioned below the medication bottle and from a medication ampoule while the selected syringe is positioned above the medication ampoule, the pumping carousel comprising syringe holder configured for holding the selected syringe, and a medication holder configured for holding the medication bottle and the medication ampoule, the carousel being further configured for rotating so that the medication bottle is positioned with a head facing up, and for rotating so that the medication bottle is positioned in an upside down position;

a medication gripper configured for inserting the medication bottle into the medication holder, for inserting the medication ampoule into the medication holder, and for breaking a head of the medication ampoule by moving while holding the head; and a syringe gripper configured for moving the selected syringe such that the needle to the syringe is dipped in medication contained in a medication ampoule, and for pumping the medication from the medication ampoule into the syringe;

an on-board computer adapted to integrate patient real time life signs data with patient information to determine in real time said medication dose; and a syringe dispensing apparatus having a syringe submission tray, the submission tray protruding from said dosage dispensing device and adapted to dispense said at least one selected syringe from said dosage dispensing device, said at least one selected syringe filled with said medication dose.

2. The device of claim 1, wherein said syringe gripper is configured to remove a needle cover from a needle coupled to a syringe prior to pumping medication into said syringe and to recover said needle with said needle cover after completion of pumping medication into said syringe.

3. The device of claim 1, wherein said real time signs data is obtained from at least one patient life-sign monitor selected from the group including consisting of an ECG monitor, an EEG monitor; a blood oxygen monitor; a patient temperature monitor; and a blood pressure monitor.

4. The device of claim 3, wherein said patient information is selected from the group consisting of a patient weight; a patient age; a patient gender; patient known allergies; a patient risk category; and medications used by said patient.

5. The device of claim 1, further comprising: a medication camera configured to verify an amount of medication in said medication bottle or medication ampoule.

6. The device of claim 1, further comprising a syringe camera configured to verify an amount of medication drawn into said syringe.

7. The device of claim 1 further configured for removing a cap covering a head of a medication bottle, wherein the pumping carousel further comprises a bottle cover remover configured for engaging a cap of a bottle, and wherein the medication gripper is configured for removing the cap by pulling the bottle while the cup is engaged in the bottle cover remover.

* * * * *